United States Patent [19]
White

[11] Patent Number: 5,205,737
[45] Date of Patent: Apr. 27, 1993

[54] ARTICULATORS FOR USE IN CONSTRUCTING ARTIFICIAL TEETH

[75] Inventor: Graham E. White, Sheffield, England

[73] Assignee: The University of Sheffield, Sheffield, England

[21] Appl. No.: 689,929

[22] Filed: Aug. 22, 1991

[30] Foreign Application Priority Data

Nov. 17, 1988 [GB] United Kingdom ............... 8826896

[51] Int. Cl.[5] .............................................. A61C 11/00
[52] U.S. Cl. ......................................... 433/55; 433/56
[58] Field of Search ...................................... 433/55, 56

[56] References Cited

U.S. PATENT DOCUMENTS

| Re. 31,615 | 6/1984 | Lee | 433/73 |
|---|---|---|---|
| 1,733,507 | 10/1929 | McCollum | 433/56 |
| 2,688,800 | 9/1954 | Gerber | 433/57 |
| 2,909,837 | 10/1959 | Gerber | 433/57 |
| 3,206,852 | 9/1965 | Swanson | 433/56 |
| 3,896,550 | 7/1975 | Lee | 433/57 |
| 4,139,946 | 2/1979 | Arant | 433/56 |
| 4,812,118 | 3/1989 | Creekmore | 433/55 |

Primary Examiner—John J. Wilson
Attorney, Agent, or Firm—Trexler, Bushnell, Giangiorgi & Blackstone, Ltd.

[57] ABSTRACT

An articulator for use in constructing artificial teeth is provided with means (10) for use in measuring the condylar movements of the artificial temporomandibular joints in the articulator, the measuring means (10) comprising boss means (11) adapted to be secured coaxially at the end of the shaft member (24) forming the pivot for a movable base plate (22) with respect to a fixed baseplate (21), axial scale bearing means (12) adapted to extend over the adjacent support (26) and generally parallel to the axis of the shaft member (24), point means (13) extending generally parallel to the axial scale bearing means (12), and slide means (14) for the pointer means (13) to enable its point (16) to be brought into contact with a scale (51) affixed to a face area of the support (26).

15 Claims, 3 Drawing Sheets

ARTICULATORS FOR USE IN CONSTRUCTING ARTIFICIAL TEETH

This invention relates to articulators for use in constructing artificial teeth and which are of the type incorporating a lower, stationary or fixed base plate and an upper, movable base plate, these base plates being connected with one another by supports.

U.S. Pat. No. 3,772,788 describes and claims such an articulator in which the supports are independently adjustable in length by up to 1.2 mm as indicated by vernier scales. It also describes the top portion of each support as being provided with a transverse bore in which is rotatably mounted a disc, and screw means to prevent axial displacement of the disc and to selectively secure the disc within a range of rotational positions as indicated by an arcuate scale, each disc also being provided with a radially extending elongated aperture in which rests a guide portion on one end of a shaft member forming a pivot for the movable base plate, and each guide portion having the form of two truncated cones which abut one another at their smaller base surfaces, as is also described in U.S. Pat. No. 2,909,837, thereby forming a waist. A movable locking element is provided on each support for optionally clamping the waist of the guide portion in engagement with the lower edge of the elongated aperture, as described and claimed in U.S. Pat. No. 2,909,837. When the locking element is not in use, tension springs between the guide portions and their respective supports urge the waists of the guide portions into centralising engagement with the lower edges of the elongated apertures.

The articulator described in U.S. Pat. No. 3,772,788 is known as the "Vario" as the relative positions of the base plates (and therefore of dentures or part dentures secured thereto) can be altered to reproduce the most complex movements of the human jaws.

A version without the length adjustment and vernier scales for each support is known as the "Individual", while another version that is also without the rotatable discs (but includes the radially extending elongated apertures in the supports) is known as the "Simplex".

The radially extending elongated apertures, cooperating guide portions on the shaft member, and tension springs are, therefore, common to all three versions of articulator and enable the condylar movements of the artificial temporomandibular joints to be observed. Hereafter, all these versions of articulator will be referred to as "of the type described".

The object of the present invention is to provide means whereby the aforesaid condylar movements can be measured.

According to the present invention, means for use in measuring the condylar movements of artificial temporomandibular joints in an articulator of the type described comprises boss means adapted to be secured coaxially at the end of the shaft member forming the pivot for the movable base plate, axial scale bearing means adapted to extend over the adjacent support and generally parallel to the axis of the shaft member, pointer means extending generally parallel to the axial scale bearing means, and slide means for the pointer means to enable its point to be brought into contact with a face area of the support when the boss means has been secured coaxially with the shaft member.

Thus, when measuring means in accordance with the invention has been secured at one end of the shaft member, the top edge of the respective support can serve as the index for the axial scale, or an index mark can be provided on that edge, and a scale can be affixed on a face area of the support for traversing by the point of the pointer means as the respective guide portion on the shaft member moves radially in its aperture in the support, the pointer means being pushed along the slide means one way or the other as the shaft member moves axially, to effect contact of the point with the scale affixed to the support.

It will be evident that an articulator of the type described will be provided with measuring means in accordance with the invention at each end of the shaft member, particularly to enable radial movements of both guide portions to be measured, the two measuring means being mirror images of each other.

The measuring means may be formed from wire, e.g., of stainless steel with round and/or flattened section, bent intermediately into an arcuate boss portion from one end of which extends a first arm to an end portion which is bent perpendicularly to form the axial scale bearing means, while from the other end of the boss portion extends a second arm with a coiled end forming the slide means for the pointer means, which may consist of a hardened steel pin with a knob on its end remote from the point. The boss portion may alternatively be formed by a complete turn of the wire, and a suitably profiled plastics washer may be provided to accommodate the overlapping portions of wire. Again, the measuring means may be manufactured in metal, e.g. stainless steel, or rigid plastics, with an annular boss and a cylindrical slide means, but being in all other respects similar to the measuring means described above.

The invention also includes an articulator having, on each end of the shaft member that forms a pivot for the movable base plate, means for measuring the condylar movements of artificial temporomandibular joints and comprising an axial scale extending over the adjacent support and generally parallel to the axis of the shaft member, pointer means extending generally parallel to the axial scale, slide means for the pointer means to enable its point to be brought into contact with a face area of the support, and a scale on that face area for traversing by the point of the pointer means as that end of the shaft member moves in simulation of the said condylar movements. Each measuring means may be formed or manufactured in any of the ways described above, and may have its boss means secured to the shaft member by the same screw that usually secures the guide portion to the shaft member, conveniently with the boss means secured between the head of the screw and the guide portion, so that the scale to be traversed by the pointer means is secured to the outside face of the respective support.

A number of embodiments of the invention will now be described by way of example only, with reference to the accompanying drawings, in which.

Figure 1:
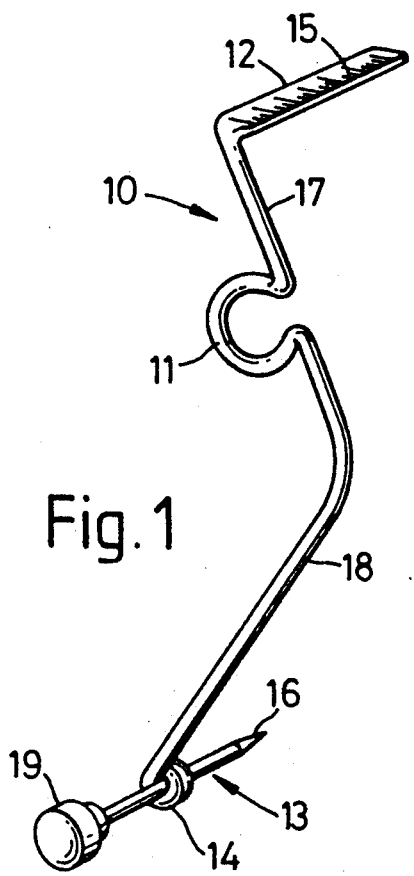
FIG. 1 is a perspective view of one form of construction of measuring means in accordance with the invention for use with an articulator, e.g., as shown in FIGS. 6 to 8.
Figure 2:
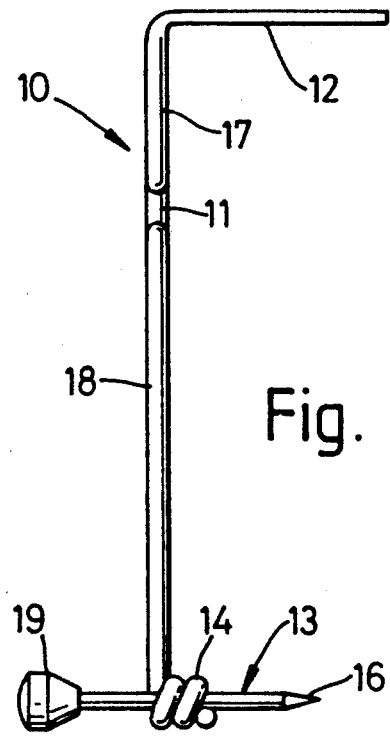
FIG. 2 is a side elevation of the measuring means of FIG. 1.
Figure 3:
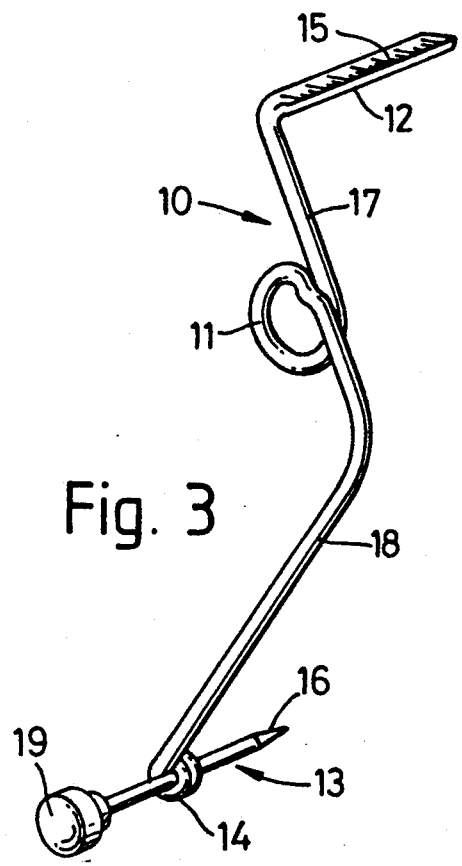
Figure 4:
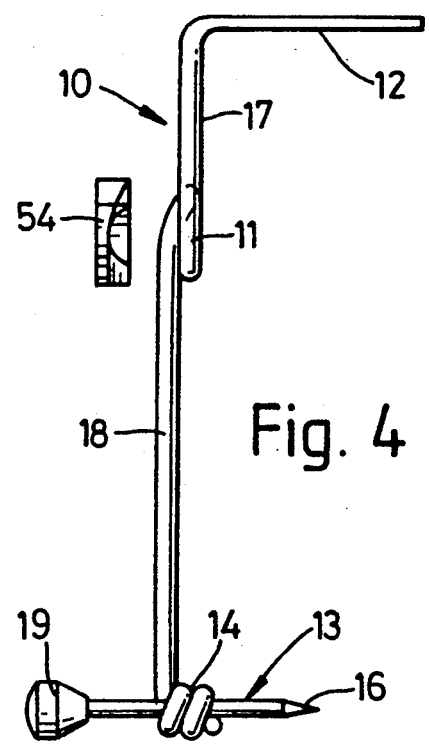
Figure 5:
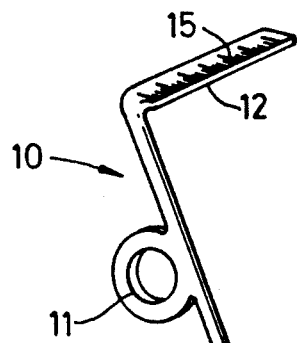
Figure 6:
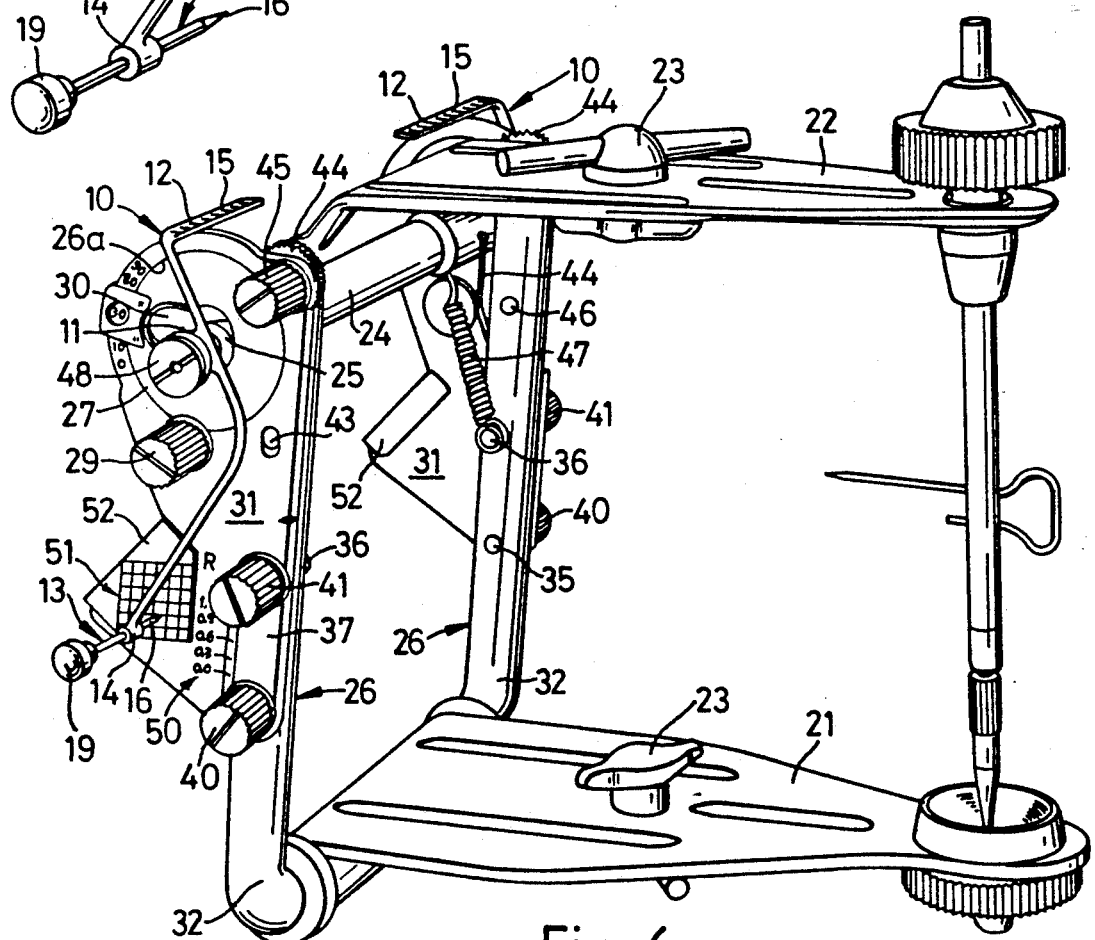
Figure 7:
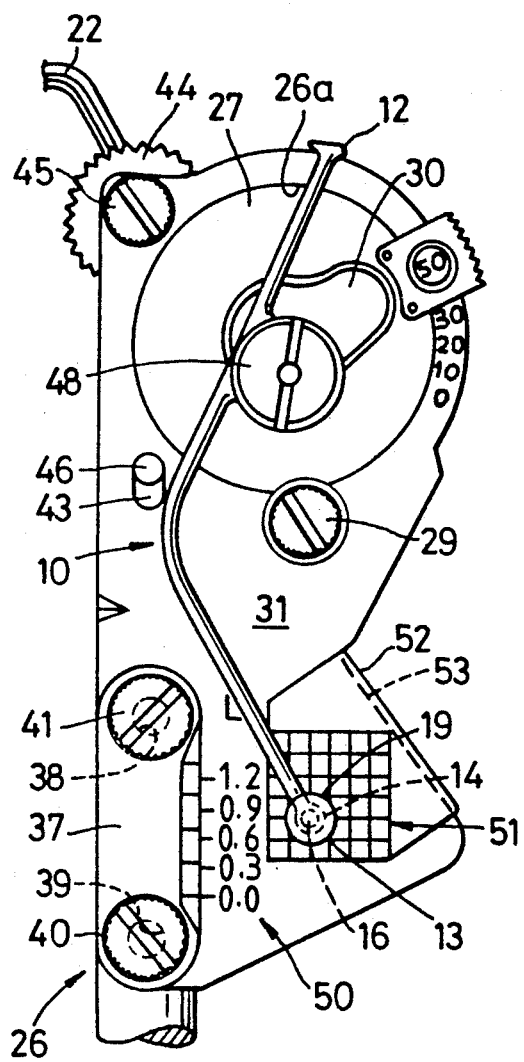
Figure 8:
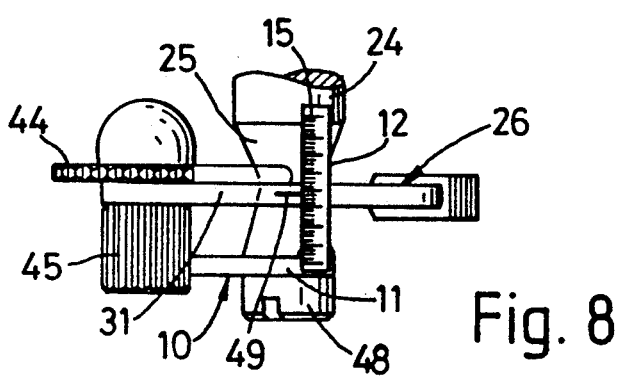

FIGS. 3 and 4 correspond to FIGS. 1 and 2 but shown another form of construction of measuring means in accordance with the invention;

FIG. 5 corresponds to FIGS. 1 and 3 but show a further form of construction of measuring means in accordance with the invention;

FIG. 6 is a perspective view of an articulator as in U.S. Pat. No. 3,772,788 which is shown fitted with measuring means as in FIG. 5;

FIG. 7 is a fragmentary elevation of the other side of the articulator of FIG. 6;

FIG. 8 is a plan view corresponding to FIG. 7; and

Figure 9:
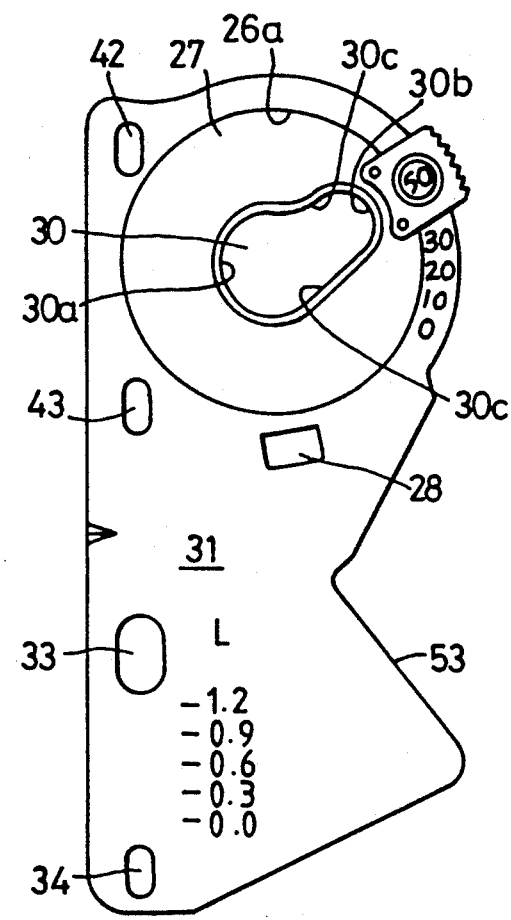

FIG. 9 corresponds to FIG. 7 but with a number of parts removed to reveal relevant details.

The measuring means 10 shown in the drawings comprises boss means 11, axial scale bearing means 12, pointer means 13, and slide means 14 for the pointer means 13, and slide means 14 for the pointer means, the purpose of which will be described after a description of the articular shown in FIG. 6 and with reference to FIGS. 7 to 9.

The articulator will be seen to embody a fixed base plate 21 and a movable base plate 22. The fixed base plate 21 and the movable base plate 22 are equipped with suitable means 23 for attaching hereto suitable impressions or reproduction of the bite of the patient. To the movable base plate 22 there is secured a shaft member 24 equipped at both ends with a respective guide portion 25. Each of those guide portions 25 possesses the configuration of a geometric body of rotation, and specifically that of two truncated cones which abut one another at their smaller base surfaces. Furthermore, the transition location between both outer surfaces or jackets of the truncated cones is advantageously slightly rounded.

Continuing, it will be recognized that the fixed base plate 21 is provided at both sides with a respective support 25 which is fixedly connected therewith. The top portion or marginal region of each support 26 is provided with a transverse bore 25a and both of these bores 26a of both supports 26 are disposed along a common horizontal axis. A disc 27 is rotatably mounted in each such bore 26a. Near the region of the transverse bore 26a there is formed a small opening 28 in the associated support 26. In each such opening 28 there is mounted a screw (not shown) and upon the shaft of such screw there is threaded an adjusting nut 29 which simultaneously serves to prevent axial displacement of the discs 27 and to selectively secure the discs 27 against rotation.

Each of the discs 27 is provided with a radially extending elongated aperture or hole 30, the boundary wall of which is a blunt knife edge in cross-section over its entire length and therefore forms a support or bearing portion for the corresponding guide portion or piece 25 which is displaceable within each such associated elongated hole 30. The periphery of the elongated hole 30 is formed from two circular arcs 30a and 30b and two tangent lines 30c which connect these circular arcs with one another. One of the circular arcs, such as arc 30a, is concentrically arranged with regard to the center of rotation of the disc 27 and possess a radius which is approximately 1.5 times greater than the smallest radius of the guide portions 25 at its transition location. The radius of the other circular arc 30b is the same size as the smallest radius of such guide portion 25.

From this relationship it will be understood that when the movable base plate 22 together with both of its guide portions or pieces 25 is supported at the lowest location of each of both support or bearing portions and thereafter the discs 27 are rotated for the purpose of changing the inclination of the lower linear section of the elongated holes 30 the guide portions or pieces 25 do not change their position because the support or bearing portion then defines a circular arc which is concentric to the axis of rotation of the dics 27.

Each of the aforementioned supports 26 consists of two components which can be displaced relative to one another, of which the respective first component 31 carries the disc 27. This disc 27 cooperates with one of the associated guide portions 25 of the movable base plate 22. The second relatively displaceable component 32 of each support 26 is directly fixedly connected in a suitable manner with the fixed base plate 21.

Now in FIG. 9 there ia again illustrated the first component 31 of each support 26 which, as shown, is constructed in the form of an elongated plate member. This plate member 31 will be seen to be provided at its lower region or terminal portion with two oppositely situated elongated holes 33 and 34. These elongated holes or apertures 33 and 34 cooperate with screws 35 and 36, which can be connected, for instance by establishing a threadable connection with the second component 32 of the support 26.

The elongated holes 33 and 34 are covered by a bracket or strap 37 which is also provided with two holes or apertures 38 and 39 which in this case however are circular. These two last-mentioned holes 38 and 39 possess a diameter which corresponds to the diameter of the screws 35 and 36 so that the bracket 37 is maintained fixed in position by these screws.

As already mentioned the screws 35 and 36 extend through the elongated holes 33 and 34 in the plate-shaped component 31 of the support 36. The large dimension of each of these elongated holes 33 and 34 is oriented in the lengthwise direction of the associated support 26. The plate-shaped component 31 of each support 26 can therefore be displaced with respect to the lower component 32 of such support 26 after releasing nuts 40 and 41 operatively associated with the screws 35 and 36. The path through which both components 31 and 32 of any given support 26 can be displaced relative to one another corresponds to the size of the lengthwise dimension of the elongated holes 33 and 34. It has been found desirable to permit a lengthwise adjustment of the supports 26 in a range of approximately zero to 1.2 millimeters.

Now the adjustment of the length of the supports 26 can take place either only at one support or at each support separately by an amount which corresponds to the examination determination or diagnosis, for instance established by X-rays. It is possible to fixed the adjusted lengths of each support 26 which has been appropriately regulated by merely tightening the associated nut members 40 and 41.

In order to be able to readily carry out the desired adjustment of the length of each of these supports in accordance with the examination results or diagnosis and specifically with the necessary accuracy, both the bracket 37 as well as the portion of each plate member 31 situated beside such bracket 37 are provided with an appropriate scale or marking, these scales collectively forming a vernier scale arrangement indicated by reference character 50. After adjusting the desired length of the support or supports 26, on the basis of the vernier scale 50 and after tightening the nut members 40 and 41 it is then possible to carry out the required adjustment work at both halves of the artificial bite.

Now in FIG. 9 there has additionally been depicted two further elongated holes or apertures 42 and 43, serving for appropriately guiding a suitable fixation or locking element 44 in the form of a toothed element. Each of these locking elements 44 can engage by means of a non-illustrated hook-shaped projection with the guide portion and so can maintain such guide portion 25 in engagement with the lower supporting or contact surface of the associated elongated hole 30. A screw 45 extends through the uppermost opening 42 and serves to secure the locking element 44 in desired position and in the next lower situated opening 43 there is mounted a guide pin 46 connected with such locking element 44.

When the locking elements 44 are not engaged with the guide portions 25, each of the latter is urged towards the lower supporting or contact surface of the associated elongated hole 30 by a tension spring 47 between the shaft member 24 and the projecting end of the screw 36. However, the tension springs 47 allow the shaft member 24 to move, axially and also transversely with respect to its axis, independent movement of each guide portion 25 in its associated elongated hole 30 being possible, to simulate comprehensively the condylar movements of temporomandibular joints.

The measuring means 10 previously referred to are adapted for use in measuring the aforesaid condylar movements, as will be described with reference to FIGS. 6 to 8. The boss means 11 is adapted to be secured coaxially at the end of the shaft member 24 forming the pivot for the movable base plate 22, by means of the same screw 48 that secures the guide portion 25 to the shaft member 24, whereby the axial scale bearing means 12 extends over the adjacent support 26 and generally parallel to the axis of the shaft member 24. An index mark 49 for the axial scale 15 is provided on the top edge of the respective support 26. The pointer means 13 extends parallel to the axial scale bearing means 12, and the slide means 14 for the point means 13 enables its point 16 to be brought into contact with a grid-like scale 51 affixed to a face area of the support 26, by being mounted on a clip 52 gripping over an edge 53 of the plate component 31 of the support 26. The scale 51 may be provided on material which can be indented by the point 16 of the pointer means 13, so as to be able to retain impressions of the pointer made before and after movement of the respective guide portion 25 radially in its aperture 30 in the support 26. The material on which the scale 51 is provided may be self-adhesive, so as to be replaceable by a fresh scale (i.e., not indented) for each patient model.

In FIGS. 1 and 2, the measuring means 10 is shown formed from wire, e.g., of stainless steel with round section, bent intermediately into an arcuate boss portion 11 from one end of which extends a first arm 17 to an end portion which is bent perpendicularly and flattened to form the axial scale bearing means 12, while from the other end of the boss portion 11 extends a second arm 18 with a coiled end forming the slide means 14 for the pointer means 13, which may consist of a hardened steel pin with a knob 19 on its end remote from the point 16.

In FIGS. 3 and 4 a wire construction as in FIGS. 1 and 2 differs only in that the boss means 11 is formed by a complete turn of the wire, and a suitably profiled plastics washer 54 (FIG. 4 only) is provided to accommodate the overlapping portions of wire.

In FIGS. 5 to 8 the (or each) measuring means 10 is manufactured in metal, e.g., stainless steel, or rigid plastics, with an annular boss 11 and a cylindrical slide means 14, but being in all other respects similar to the measuring means of FIGS. 1 and 2 or FIGS. 3 and 4.

A friction washer (not shown) may be interposed between the (or each) boss means 11 and the associated guide portion 25 on the shaft member 24, to secure the measuring means 10 against rotation relative to that guide portion and the shaft member.

I claim:

1. Means for use in measuring the condylar movements of artificial temporomandibular joints in an articulator of the type incorporating a lower, stationary base plate and an upper, movable base plate, these base plates being connected with one another by supports the top portion of each of which has a transverse bore in which is rotatably mounted a disc, and screw means to prevent axial displacement of the disc and to selectively secure the disc within a range of rotational positions as indicated by an arcuate scale, each disc also being provided with a radially extending elongated aperture in which rests a guide portion on one end of a shaft member forming a pivot for the movable base plate, and each guide portion having the form of two truncated cones which abut one another at their smaller base surfaces, thereby forming a waist urged into centralising engagement with the lower edges of the elongated apertures by tension springs between the guide portions and their respective supports;

the said measuring means comprising a boss adapted to be secured coaxially at one end of the shaft member forming the pivot for the movable base plate, a first arm extending from the boss, axial scale bearing means adapted to extend from the first arm over the adjacent support and generally parallel to the axis of the shaft member, a second arm extending from the boss, a pointer extending generally parallel to the axial scale bearing means, and slide means on the second arm for the pointer to enable its point to be brought into contact with a face area of the support when the boss has been secured coaxially with the shaft member.

2. Measuring means as in claim 1, formed from wire being intermediately into an arcuate boss portion from one end of which extends the first arm to an end portion which is bent perpendicularly to form the axial scale bearing means, while from the other end of the arcuate boss portion extends the second arm with a coiled end forming the slide means for the pointer.

3. Measuring means as claim 2, wherein the boss is formed by a complete turn of wire.

4. Measuring means as in claim 1 manufactured in metal or rigid plastics, with an annular boss portion and a cylindrical slide means.

5. Measuring means as in claim 1, wherein the pointer consists of a hardened steel pin with a knob on its end remote from its point.

6. An articulator of the type incorporating a lower, stationary base plate and an upper, movable base plate, these base plates being connected with one another by supports the top portion of each of which has a transverse bore in which is rotatably mounted a disc, and screw means to prevent axial displacement of the disc and to selectively secure the disc within a range of rotational positions as indicated by an arcuate scale, each disc also being provided with a radially extending elongated aperture in which rests a guide portion on one end of a shaft member forming a pivot for the movable base plate, and each guide portion having the form of two truncated cones which abut one another at their smaller base surfaces, thereby forming a waist urged into centralising engagement with the lower edges of the elongated apertures by tension springs between the guide portions and their respective supports;

the said articulator having on each end of the shaft member that forms a pivot for the movable base plate, means for measuring the condylar movements of artificial temporomandibular joints and comprising an axial scale extending over the adjacent support and generally parallel to the axis of the shaft member, an index mark for the axial scale on the support, a pointer extending generally parallel to the axial scale, slide means for the pointer to enable its point to be brought into contact with a face area of the support, and a scale on that face area for traversing by the point of the pointer as that end of the shaft member moves in simulation of the said condylar movements.

7. An articulator as in claim 6, wherein a grid-like scale is affixed to the face area of the respective support traversed by the pointer.

8. An articulator as in claim 7, wherein the grid-like scale is mounted on a clip gripping over an edge of the support.

9. An articulator as in claim 7, wherein the grid-like scale is provided on material able to retain impressions of the point of the pointer means.

10. An articulator as in claim 7, wherein the grid-like scale is provided on self-adhesive material, so as to be replaceable by a fresh scale for each patient model.

11. An articulator as in claim 6, wherein the axial scale extends from a first arm extending radially from the respective end of the shaft member, and the slide means is provided on a second arm extending radially from said respective end of the shaft member.

12. An articulator as in claim 11, wherein each measuring means has a boss secured to the respective end of the shaft member, and from which boss the first and second arms extend radially to the axial scale and the slide means respectively.

13. An articulator as in claim 12, wherein the boss of each measuring means is secured to the shaft member by the screw that secures the guide portion to the shaft member.

14. An articulator as in claim 13, wherein the boss is secured between the head of the screw and the guide portion.

15. An articulator as in claim 13, wherein a friction washer is interposed between each boss and the associated guide portion on the shaft member.

* * * * *